US00PP07987P

United States Patent [19]

Saville

[11] Patent Number: Plant 7,987

[45] Date of Patent: Sep. 29, 1992

[54] MINIATURE ROSE PLANT NAMED SAVAFACE

[75] Inventor: F. Harmon Saville, Rowley, Mass.

[73] Assignee: Nor'East Miniature Roses, Inc., Rowley, Mass.

[21] Appl. No.: 639,251

[22] Filed: Jan. 8, 1991

[51] Int. Cl.[5] ..... A01H 5/00

[52] U.S. Cl. ..... Plt./9

[58] Field of Search ..... Plt./9, 10, 7

[56] References Cited

U.S. PATENT DOCUMENTS

P.P. 4,811 1/1982 Saville ..... Plt. 10

*Primary Examiner*—Howard J. Locker

*Attorney, Agent, or Firm*—Christie, Parker & Hale

[57] ABSTRACT

A new miniature rose with rosy pink flowers of good form.

1 Drawing Sheet

SUMMARY OF THE INVENTION

The present invention relates to a new and distinct variety of rose plant of the miniature rose class, which was created by me by crossing as seed parent an unnamed, unpatented seedling of my creation and as pollen parent the rose known as 'Mountie' (U.S. Plant Pat. No. 6,054). The varietal denomination of this new rose is 'Savaface'.

Among the novel characteristics prossessed by this new variety which distinguishes it from its parents and all other varieties of which I am aware is its rosy pink flowers of good form and which holds the color well.

Asexual reproduction by propagation by cuttings of the new variety as performed in Essex County, Mass. shows that the foregoing and other distinguishing characteristics come true to form and are established and transmitted through succeeding propagations.

BRIEF DESCRIPTION OF ILLUSTRATION

The accompanying illustration shows typical specimens of the vegetative growth and flowers of the new variety in different stages of development depicted in color as nearly true as it is reasonably possible to make the same in a color illustration of this character.

DETAILED DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart.

Parentage:

*Seed parent.*—Unnamed seedling.

*Pollen parent.*—'Mountie'.

Class: Miniature.

The following observations are made of specimens grown under glass in Essex County, Mass., during the month of November.

FLOWER

Blooming habit: Continuous.

A. Bud:

(1) *Size.*—Medium.

(2) *Form.*—Ovate.

(3) *Color.*—As sepals divide, bud color is near 58C.

(4) *Sepals.*—Smooth, longer than bud.

(5) *Peduncle.*—Length — about 1 to 1⅛ inches. Aspect — straight. Strength — erect. Color — near 146D.

B. Bloom:

(1) *Size.*—Average size when fully expanded — about 1 to 1¼ inches.

(2) *Borne.*—Singly, one to a stem and in small sprays.

(3) *Form.*—High centered at first; outer petals quill to points and roll under.

(4) *Petalage.*—Number of petals under normal conditions — about 35 to 40.

(5) *Color.*—After sepals fall and petals unfurl, predominant flower color is near 54A to B to 58C. Flowers retain the clean coloration as petals open. Deeper hues may be seen where petals bunch. Consistent coloring remains after three or more days with only slight lightening. General tonality from a distance is rosy pink. Color at point of petal attachment is near 2D.

C. Petals:

(1) *Texture.*—Thick.

(2) *Appearance.*—Inside velvety and outside satiny.

(3) *Form.*—Wide, fan shaped; some pointed apices.

(4) *Arrangement.*—Regularly arranged, imbricated.

(5) *Petaloids in center.*—Medium.

(6) *Persistence.*—Long lasting.

(7) *Fragrance.*—None.

(8) *Lasting quality.*—Lasting quality on plant is very long, slightly less as cut flower.

REPRODUCTIVE ORGANS

A. Stamens, filaments and anthers:

*Arrangement and color.*—Regularly arranged around styles. Color — near 15C.

B. Pollen:

*Color.*—Near 15B.

C. Styles: Thin, few.

D. Stigmas:

*Color.*—Near 154D.

E. Hips: None observed.

PLANT

A. Form: Compact, symmetrical.

B. Growth: Very vigorous, uniform branching.
*Height attained.*—About 12 to 16 inches.

C. Foliage: Compound 5 to 7 leaflets.
(1) *Size.*—Medium.
(2) *Quantity.*—Abundant.
(3) *Color.*—New foliage: Upper side — near 137A. Under side — near 138B. Old foliage: Upper side — near 137A. Under side — near 138B.
(4) *Shape.*—Oval, pointed.
(5) *Texture.*—Upper side is glossy; under side is matte.
(6) *Edge.*—Serrate.
(7) *Serration.*—Fine, regular.
(8) *Leaf Stem.*—Color — near 148B. Under side — 148C.
(9) *Stipules.*—Medium length, not bearded.
(10) *Resistance to disease.*—Blackspot — Good. Mildew — Good. Rust — Good.

D. Wood:

(1) *New wood.*—Color — near 146C. Bark — smooth.
(2) *Old wood.*—Color — near 146B. Bark — smooth.

E. Thorns:
*Quantity (main stalk).*—Few.
*On laterals from stalk.*—Few.
*Form.*—Short, thin, straight, pointed.
*Length.*—3/16 to $\frac{1}{4}$ inches.
*Color.*—near 181A.
*Position.*—Irregular.
*Prickles.*—Few.

F. Winter hardiness: Needs protection in severe climates.

I claim:

1. A new and distinct variety of rose plant of the miniature rose class, substantially as shown and described.

* * * * *

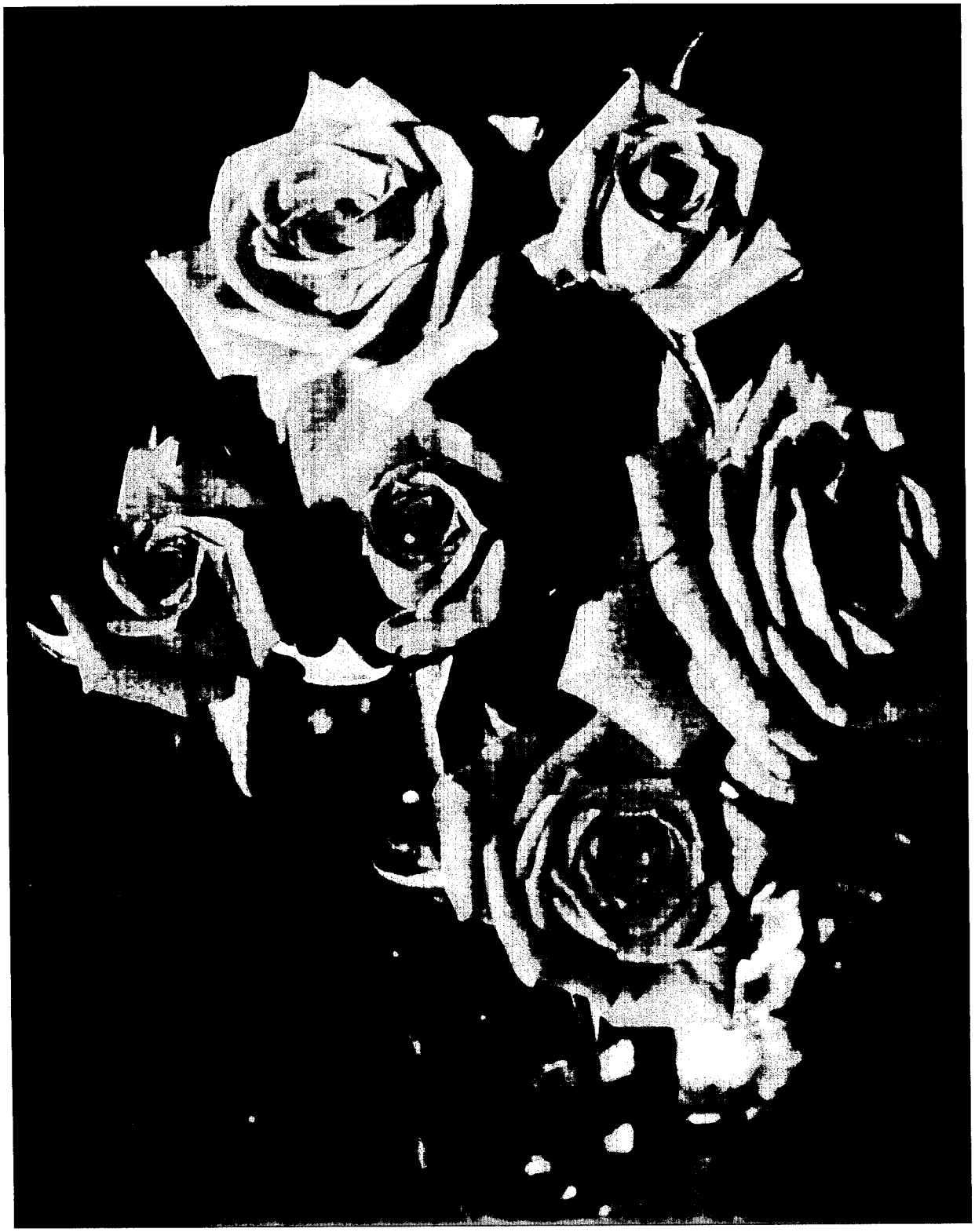

UNITED STATES PATENT AND TRADEMARK OFFICE

CERTIFICATE OF CORRECTION

PATENT NO. : Plant 7,987

DATED : September 29, 1992

INVENTOR(S) : F. Harmon Saville

It is certified that error appears in the above-identified patent and that said Letters Patent is hereby corrected as shown below:

Column 1, line 10, change "prosessed" to -- possessed --.

Signed and Sealed this

Fourteenth Day of December, 1993

*Attest:*

Bruce Lehman

BRUCE LEHMAN

*Attesting Officer*

*Commissioner of Patents and Trademarks*